United States Patent [19]
Hesse et al.

[11] Patent Number: 5,853,976
[45] Date of Patent: Dec. 29, 1998

[54] **RECOMBINANT PROTEINASE FROM *CLOSTRIDIUM HISTOLYTICUM* AND ITS USE FOR ISOLATING CELLS AND GROUPS OF CELLS**

[75] Inventors: Friederike Hesse; Dorothee Ambrosius, both of München; Helmut Burtscher, Habach, all of Germany

[73] Assignee: Boehringer Mannheim GmbH, Mannheim, Germany

[21] Appl. No.: 849,536

[22] PCT Filed: Dec. 20, 1995

[86] PCT No.: PCT/EP95/05054

§ 371 Date: Aug. 26, 1997

§ 102(e) Date: Aug. 26, 1997

[87] PCT Pub. No.: WO96/19583

PCT Pub. Date: Jun. 27, 1996

[30] Foreign Application Priority Data

Dec. 22, 1994 [DE] Germany ............................ 44 45 891

[51] Int. Cl.$^6$ .............................. C12Q 1/00; C12P 21/06; C07H 17/00; C12N 9/00
[52] U.S. Cl. .......................... 435/4; 435/69.1; 435/320.1; 435/252.3; 435/325; 435/183; 435/254.2; 435/252.8; 435/219; 536/23.1
[58] Field of Search .......................... 435/4, 69.1, 320.1, 435/252.3, 325, 183, 254.2, 252.8, 219; 536/23.1

[56] References Cited

PUBLICATIONS

Wolters, et al., *Diabetologia*, vol. 35, 1992, pp. 735–742, "An analysis of the role of collagenase and protease in the enzymatic dissociation of the rat pancrease for islet isolation".

Hefley, et al., *Experimental Cell Research*, vol. 149, 1983, pp. 227–236, "Enzymatic isolation of cells from neonatal calvaria using two purified enzymes from Clostridium histolyticum".

Wetmore, et al., *Molecular Microbiology*, vol. 6, 1991, pp. 1593–1604, "The role of the pro–sequence in the production and secretion of the thermolysin–like neutral protease form *Bacillus cereus*".

Meinhardt, et al., *Appl. Microbiol. Biotechnol.*, vol. 41, 1994, pp. 344–351, "Cloning and sequencing of the leuC and npr genes and a putative spo IV gene from *Bacillus megaterium* DSM319".

*Primary Examiner*—Karen Cochrane Carlson
*Attorney, Agent, or Firm*—Nikaido Marmelstein Murray & Oram, LLP

[57] ABSTRACT

Process for disintegrating cell tissue and releasing cells or groups of cells contained therein by incubating the cell tissue with a recombinant neutral protease from *Clostridium histolyticum* which is coded by a) a DNA of nucleotides 1027–1965 from SEQ ID NO:3 or a DNA which is complementary thereto, b) nucleic acids which hybridize with a DNA of nucleotides 1027–1965 from SEQ ID NO:3, c) nucleic acids which, without the degeneracy of the genetic code, would hybridize with one of the nucleic acids mentioned in a) or b)

and is the product of a prokaryotic or eukaryotic expression of an exogenous nucleic acid, until the cells or groups of cells have been released to the desired extent and separating the cells or groups of cells from the cell tissue fractions.

17 Claims, 1 Drawing Sheet

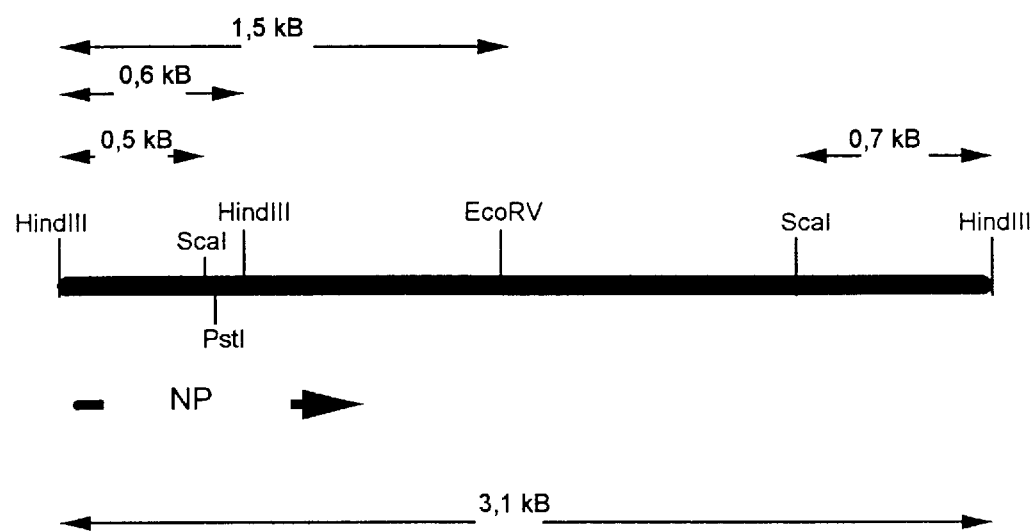

RECOMBINANT PROTEINASE FROM *CLOSTRIDIUM HISTOLYTICUM* AND ITS USE FOR ISOLATING CELLS AND GROUPS OF CELLS

The invention concerns a recombinant proteinase (neutral protease, NP) from *Clostridium histolyticum* and its use for isolating cells and groups of cells.

Proteolytic enzymes from *Clostridium histolyticum* are used to digest tissues and to isolate individual cells or groups of cells (e.g. islets) (islets: Sutton et al., Transplantation 42 (1986) 689–691; liver: Quibel et al., Anal. Biochem. 154 (1986) 26–28; bones: Hefley et al., J. Bone Mineral Res. 2 (1987) 505–516; Holzinger et al., Immunology Letters 35 (1993) 109–118). Two different collagenase types are known from *Clostridium histolyticum* (M. F. French et al., J. Protein Chemistry 11 (1992) 83–97).

In addition to various isoforms of type I and type II collagenase, a neutral protease (NP) from *Clostridium histolyticum* is also known the activity optimum of which is in the neutral pH range and which cleaves casein as well as denatured collagen (Azocoll) (Mandl et al., J. Clin. Invest 32, 1953, 1323–1329; Sparrow & McQuade, Biochim. Biophys. Acta 302, 1973, 90–94; Hefley, J. Bone Mineral Res. 2, 1987, 505–516). This neutral protease is regarded as being necessary as an auxiliary enzyme in the digestion of various tissues (bones: Hefley et al., Exp. Cell Res. 149, 1983, 227–236; pancreas: Wolters et al., Diabetologica 35, 1992, 735–742). NP has a molecular weight of ca. 35 kD (SDS gel electrophoresis).

In order to use neutral protease to isolate cells and groups of cells on a large scale it is necessary to provide the neutral protease in a reproducible quality and in large amounts. This is possible by recombinant production processes.

Therefore the object of the present invention was to provided nucleic acids which code for proteins with the activity of the neutral protease from *Clostridium histolyticum* as well as a process for their recombinant production.

The object is achieved by a nucleic acid which codes for a protein with the activity of the neutral protease from *Clostridium histolyticum* which is characterized in that it is selected from the group comprising a) a DNA of nucleotides 1027–1965 from SEQ ID NO:3 or a DNA which is complementary thereto, b) nucleic acids which hybridize with a DNA of nucleotides 1027–1965 from SEQ ID NO:3, c) nucleic acids which, without the degeneracy of the genetic code, would hybridize with one of the nucleic acids mentioned in a) or b).

A nucleic acid is preferred of nucleotides 1027–1965 from SEQ ID NO:3. Nucleic acids are also suitable which, compared to this nucleic acid, are shortened or extended preferably at the 5' end by for example ca. 60 nucleotides. An extended nucleic acid of nucleotides 970–1965 is particularly preferred which corresponds to a proform of the protease. Shortened nucleic acids correspond to proteolytically, preferably autoproteolytically, processed proteins.

The activity of neutral protease is known to a person skilled in the art and described by Mandle et al. (1953) Sparrow and McQuade (1973) and Hefley (1987). Neutral protease cleaves casein as well as denatured collagen.

Hybridization within the sense of the invention is understood as a hybridization under the usual stringent conditions familiar to a person skilled in the art as they are for example stated by J. Sambrook in Molecular Cloning, Cold Spring Harbor Laboratory (1989) and B. D. Hames, S. G. Higgins, Nucleic Acid Hybridization—A practical approach (1985), IRL-Press, Oxford, England. Usually the standard protocols are used for the hybridization which are described in these publications.

"Stringent conditions" are preferably understood as a hybridization in 6.0×SSC at about 45° C. with a subsequent washing step at 2.0×SSC at 50° C. In order to adjust the stringency the salt concentration can for example be selected in the washing step of 2.0×SSC at 50° C. for low stringency to 0.2×SSC at 50° C. for high stringency. In addition the temperature of the washing step can be set between room temperature (22° C., low stringency) to about 65° C. (high stringency). The stringent hybridization conditions are preferably selected such that at least a homology of 75% preferably of 90% is obtained in the amino acid sequence.

A DNA or RNA is suitable within the sense of the invention as a nucleic acid. In this case the RNA is complementary to a DNA according to the invention. The nucleic acid according to the invention can be of synthetic, semi-synthetic or recombinant origin.

It has turned out that the usual processes for cloning neutral protease cannot be used. If after purification of the neutral protease peptide sequences are determined and degenerate DNA sequences are derived therefrom in the usual manner, sequences are obtained which, as oligonucleotides, lead to the isolation of fragments in PCR reactions which do not code for proteins that have a neutral protease activity.

For example the peptide sequences NP23 (SEQ ID NO:8 in which Asp can also be in position 3 instead of Ala) and NP44 (SEQ ID NO:4) were derived from the partial sequencing of the neutral protease. Using degenerate primers which are derived from these peptides a 300 bp fragment is obtained in the PCR reaction that does not code for a neutral protease. Using a degenerate primer derived from peptide NP44 alone one obtains a fragment of about 400 bp in size which also does not code for the neutral protease. Also the use of primer 86-1F (SEQ ID NO:11) based on the peptide NP86 (SEQ ID NO:10) results in a 350 bp fragment that is unrelated to neutral protease.

Hence screening with primers derived from peptide sequences does not simply lead to usable results in the case of neutral protease.

Surprisingly, however, a combination of primers 23F (SEQ ID NO:9) and 86-1R (SEQ ID NO:12) resulted in a ca. 320 bp fragment which is part of neutral protease gene and can be used to label and screen. However, even with the aid of this labelled part it was not possible to fish out clones with further parts of the neutral protease gene. It was not until further modification of the cloning process that it was possible to find the coding DNA.

The production of the recombinant protease can be carried out according to methods familiar to a person skilled in the art. For this a DNA is firstly produced which is capable of producing a protein which has the activity of the protease. Such a DNA which is selected from the group comprising a) a DNA of nucleotides 1027–1965 from SEQ ID NO:3 or a DNA which is complementary thereto, b) nucleic acids which hybridize with a DNA of nucleotides 1027–1965 from SEQ ID NO:3, c) nucleic acids which, without the degeneracy of the genetic code, would hybridize with one of the nucleic acids mentioned in a) or b)

is selected and inserted into an expression vector. Such a vector contains promoter/operator elements which are necessary to express the DNA in addition to the NP sequence. This vector which contains the NP sequence and the promoter/operator elements is transferred into a host strain which is capable of expressing the DNA of NP. The host cell is cultured under conditions which are suitable for the amplification of the vector and NP is isolated. In this process suitable measures ensure that the protein can adopt an active tertiary structure in which it exhibits NP properties.

In this process it is not necessary that the expressed protein contains the exact NP amino acid sequence as shown in SEQ ID NO: 5. Proteins are equally suitable which contain essentially the same sequence and have analogous properties. SEQ ID NO:1 and SEQ ID NO:2 show preferred DNA fragments. A DNA of nucleotides 1027–1965 from SEQ ID NO:3 is preferred. Nucleic acids are also suitable which compared to this sequence are shortened or extended for example by preferably ca. 60 nucleotides preferably at the 5' end. An extended nucleic acid of nucleotides 970–1965 is especially preferred which corresponds to a proform of the protease. Shortened nucleic acids correspond to proteolytically, preferably autoproteolytically, processed proteins.

The nucleic acid sequence of the protein can also be modified. Such modifications are for example:

Modification of the nucleic acid in order to introduce various recognition sequences of restriction enzymes to facilitate the steps of ligation, cloning and mutagenesis.

Modification of the nucleic acid to incorporate preferred codons for the host cell.

Extension of the nucleic acid by additional operator elements in order to optimize the expression in the host cell.

The invention in addition concerns a process for the production of a polypeptide which has the properties of an NP from *Clostridium histolyticum* by expression of an exogenous nucleic acid in prokaryotic or eukaryotic host cells and isolation of the desired polypeptide wherein the DNA which codes for the said peptide is selected from the group comprising:

a) a DNA of nucleotides 1027–1965 from SEQ ID NO:3 or a DNA which is complementary thereto, b) nucleic acids which hybridize with a DNA of nucleotides 1027–1965 from SEQ ID NO:3, c) nucleic acids which, without the degeneracy of the genetic code, would hybridize with one of the nucleic acids mentioned in a) or b).

A DNA of nucleotides 1027–1965 from SEQ ID NO:3 is preferably used. A biologically functional plasmid or a viral DNA vector is used for the expression which contains a nucleic acid according to the invention. A eukaryotic or prokaryotic host cell is stably transformed or transfected with this vector.

The protein is preferably expressed in microorganisms, in particular in prokaryotes and in this case in *E. coli*.

The expression vectors must contain a promoter which enables the expression of the protein in the host organism. Such promoters are known to a person skilled in the art and are for example the lac promoter (Chang et al., Nature 198 (1977) 1056), trp (Goeddel et al., Nuc. Acids Res. 8 (1980) 4057), $\lambda_{PL}$ promoter (Shimatake et al., Nature 292 (1981) 128) and T5 promoter (U.S. Pat. No. 4,689,406). Synthetic promoters are also suitable such as for example the tac promoter (U.S. Pat. No. 4,551,433). Coupled promoter systems are also suitable such as the T7-RNA polymerase/promoter system (Studier et al., J. Mol. Biol. 189 (1986) 113). Hybrid promoters composed of a bacteriophage promoter and the operator region of the microorganism (EP-A 0 267 851) are equally suitable. An effective ribosome binding site is necessary in addition to the promoter. In the case of *E. coli* this ribosome binding site is denoted the Shine-Dalgarno (SD) sequence (Sambrook et al., "Expression of cloned genes in *E. coli*" in Molecular Cloning: A laboratory manual (1989) Cold Spring Harbor Laboratory Press, New York, USA).

In order to improve the expression it is also possible to express the protein as a fusion protein. In this case a DNA sequence which codes for the N-terminal part of an endogenous bacterial protein or for another stable protein is usually fused to the 5' end of the DNA coding for the NP. Examples of this are for example lacZ (Phillips and Silhavy, Nature 344 (1990) 882–884), trpE (Yansura, Meth. Enzymol. 185 (1990) 161–166).

The fusion proteins obtained after expression are preferably cleaved with enzymes (e.g. factor Xa) (Nagai et al., Nature 309 (1984) 810). Further examples of cleavage sites are the IgA protease cleavage site (WO 91/11520, EP-A 0 495 398) and the ubiquitin cleavage site (Miller et al., Bio/Technology 7 (1989) 698).

The proteins expressed in this manner in bacteria are isolated in the usual way by lysing the bacteria and protein isolation.

In a further embodiment it is possible to secrete the proteins as active proteins from the microorganisms. For this a fusion product is preferably used which is composed of a signal sequence which is suitable for the secretion of proteins in the host organisms used and the nucleic acid which codes for the protein. In this process the protein is either secreted into the medium (in the case of gram-positive bacteria) or into the periplasmatic space (in the case of gram-negative bacteria). It is expedient to place a cleavage site between the signal sequence and the sequence coding for the NP which enables cleavage of the protein either during processing or in an additional step. Such signal sequences are derived for example from ompA (Ghrayeb et al. EMBO J. 3 (1984) 2437) or phoA (Oka et al., Proc. Natl. Acad. Sci. USA 82 (1985) 7212).

The vectors in addition also contain terminators. Terminators are DNA sequences which signal the end of a transcription process. They are usually characterized by two structural features: an inverse repetitive G/C-rich region which can intramolecularly form a double helix and a number of U(or T) residues. Examples are the trp attenuator and terminator in the DNA of the phages fd and rrnB (Brosius et al., J. Mol. Biol. 148 (1981) 107–127).

In addition the expression vectors usually contain a selectable marker in order to select the transformed cells. Such selectable markers are for example the resistance genes for ampicillin, chloroamphenicol, erythromycin, kanamycin, neomycin and tetracyclin (Davies et al., Ann. Rev. Microbiol. 32 (1978) 469). Selectable markers which are also suitable are the genes for substances that are essential for the biosynthesis of substances necessary for the cell such as e.g. histidine, tryptophan and leucine.

Numerous suitable bacterial vectors are known. Vectors have for example been described for the following bacteria: Bacillus subtilis (Palva et al., Proc. Natl. Acad. Sci. USA 79 (1982) 5582), *E. coli* (Aman et al., Gene 40 (1985) 183; Studier et al., J. Mol. Biol. 189 (1986) 113), Streptococcus cremoris (Powell et al., Appl. Environ. Microbiol. 54 (1988) 655), *Streptococcus lividans* and *Streptomyces lividans* (U.S. Pat. No. 4,747,056).

Further genetic engineering methods for the construction and expression of suitable vectors are described in J. Sambrook et al., Molecular Cloning: A laboratory manual (1989), Cold Spring Harbor Laboratory Press, New York, N.Y.

Apart from in prokaryotic microorganisms, recombinant NP can also be expressed in eukaryotes (such as for example CHO cells, yeast or insect cells). The yeast system or insect cells are preferred as the eukaryotic expression system. Expression in yeast can be achieved by means of three types of yeast vectors: integrating $YI_p$ (yeast integrating plasmids) vectors, replicating $YR_p$ (yeast replicon plasmids) vectors and episomal $YE_p$ (yeast episomal plasmids) vectors. More details of this are for example described in S. M. Kingsman et al., Tibtech 5 (1987) 53–57).

The invention in addition concerns a process for disintegrating cell tissue and the release of cells or groups of cells contained therein by incubating the cell tissue with a neutral protease from Clostridium histolyticum which is coded by
  a) a DNA of nucleotides 1027–1965 from SEQ ID NO:3 or a DNA which is complementary thereto,
  b) nucleic acids which hybridize with a DNA of nucleotides 1027–1965 from SEQ ID NO:3,
  c) nucleic acids which, without the degeneracy of the genetic code, would hybridize with one of the nucleic acids mentioned in a) or b)
and is the product of a prokaryotic or eukaryotic expression of an exogenous DNA, until the cells or groups of cells have been released to the desired extent and separating the cells or groups of cells from the cell tissue fractions. Due to the recombinant production in a host cell which is different from Clostridium histolyticum, this protease is free from other proteins from Clostridium histolyticum. The separation of the cells or groups of cells from the cell tissue fractions is preferably carried out by centrifugation using a density gradient.

A protease is preferably used which is coded by nucleotides 1027–1965 of SEQ ID NO:3 or a form extended or shortened N-terminally by ca. 20 amino acids. An extended protease is particularly preferred which is coded by DNA of the nucleotides 970–1965 of SEQ ID NO:3 and corresponds to a proform of the protease. Such an extended protease is degraded during transport through the membrane into the periplasma or into the medium by signal peptidases to a shortened form (e.g. a protein with the amino acid sequence SEQ ID NO:5). N- or C-terminally shortened forms are also preferred which can for example be formed autocatalytically.

Cells or groups of cells are usually isolated from tissues (e.g. pancreas, liver, skin, endothelium, umbilical cord, bones) by incubating organs, parts of organs or tissues with enzymes which dissolve the surrounding extracellular connective tissue matrix (islets: Sutton et al., Transplantation 42 (1986) 689–691; liver: Quibel et al., Anal. Biochem. 154 (1986) 26–28; bones: Hefley et al., J. Bone Mineral Res. 2 (1987) 505–516).

The proteinase according to the invention can also be used for the preparation of muscle cells (Maruyama et al., J. Pharmacol. Methods 19, 1988, 155–164), fat cells (Vendrell & Alemany, J. Biochem. Biophys. Methods 16, 1988, 49–54), ovary or uterus tissue (Marcus et al., Endocrine Res. 10, 1984, 151–162), epithelial cells (Kaunitz, Am. J. Physiol. 254, 1988, 6502–6512), heart cells (Haworth et al., Cell Calcium 10, 1989, 57–62) and placental tissue (Morrish & Siy, Endocrine Res. 12, 1986, 229–253).

Tissue disintegration can also be carried out by perfusing the entire organ (Ricordi et al., Diabetes 37 (1988) 413–420) with an enzyme solution. Important factors in this process, in addition to the composition of the enzyme mixture, are the duration, the pH value and the temperature of the digestion as well as the mechanical action e.g. by shaking and addition of metal balls. Since extracellular connective tissue matrix often has a high proportion of collagen, collagenases and the neutral proteinase play a special role (Wolters, Hormone and Metabolic Research 26 (1994), p. 80).

The process according to the invention is preferably used to isolate islets or islet cells from pancreatic tissue.

Further preferred applications are the isolation of cells from tissues of all kinds to set up cell cultures or to isolate cells which are used for gene therapeutic or cell therapeutic purposes (cell engineering). The proteinase according to the invention and the process according to the invention can also be used to dissociate tumour tissue, preferably ex vivo. In this case the tumour cells isolated in this manner are for example returned to the patient after genetic modification in order to affect an immunization against the tumour for example doe an adoptive immune therapy.

In addition the addition of further enzymes such as collagenases, elastase, trypsin, chymotrypsin or hyaluronidase may be advantageous for the quality of the digestion.

The deposited plasmids as well as the following examples, publications, the sequence protocol and the FIGURE further elucidate the invention the protective scope thereof results from the patent claims. The processes described are to be understood as examples which also describe the subject matter of the invention even after modification.

The plasmid pNP-86-1R/23F was deposited on the Dec. 9, 1994 at the "Deutsche Sammlung von Mikroorganismen und Zellkulturen GmbH (DSM), Mascheroder Weg 1b, D-38124 Braunschweig under the number DSM 9578.

The plasmid pUC21-E-NP that contains the bases 933–2100 of SEQ ID NO:3 was deposited on the Nov. 23, 1995 at the "Deutsche Sammlung von Mikroorganismen und Zellkulturen GmbH (DSM), Mascheroder Weg 1b, D-38124 Braunschweig" under the number DSM 10341.

FIG. 1 shows a rough restriction map of the neutral protease.

The sequence protocols denote:
SEQ ID NO: 1: DNA fragment of the neutral protease
SEQ ID NO: 2: DNA fragment of the neutral protease
SEQ ID NO: 3: DNA of the neutral protease with flanking regions
SEQ ID NO: 5: protein sequence of neutral protease
SEQ ID NO: 4, 8, 10, 13, 14 and 16: peptides used to derive primers
SEQ ID NO: 6, 7, 9, 11, 12, 15, 17–20: primer sequences

EXAMPLE 1

Isolation of neutral protease
Purification of NP from the culture supernatant of Clostridium histolyticum A collagenase P lyophilisate (BM/Order No. 1213857) was dissolved in 5 mM HEPES buffer, pH 7.5, 1 mM $CaCl_2$ and centrifuged. The supernatant was pumped onto a Q-Sepharose column that had been equilibrated with the same buffer (loading: max. 20 mg lyo/ml column material). After washing the column with equilibration buffer until the base line was reached, the NP was eluted with an increasing $CaCl_2$ gradient (1–150 mM, 10-fold). The fractions with a high caseinolytic activity (resorufin-casein) were pooled. A clear band can be recognized at ca. 33 kD on the SDS gel, visible bands appear at ca. 50 kD (lot-dependent) as impurities as well as in the lower molecular range (<10 kD) in addition to a "brown pigment".

The NP fraction is applied at 4° C. to a butyl 650C column (equilibrated with 10 mM Tris, pH 7.5, 5 mM $CaCl_2$). Under these conditions NP is bound to the hydrophobic column material while the impurities (brown pigment, double band at ca. 50 kD) are located in the eluant. It is eluted at 4° C. with 10 mM Tris, pH 8.3, 5 mM $CaCl_2$ and 10% isopropanol or 30% isopropanol. The protein obtained in this way is homogeneous according to SDS-PAGE (>95% pure). This highly pure NP preparation (100-fold increase in the specific activity with resorufin-casein) was digested with trypsin and the peptides were separated by means of a reversed phase HPLC column (C8). The amino acid sequence was determined after concentrating the peptides to dryness.

EXAMPLE 2

Cloning neutral protease

The matching (degenerate) DNA sequence is derived from the peptide sequences determined according to example 1 after purification of the neutral protease. Sequences which exhibit an advantageous (low) denaturation are used to construct a labelled DNA probe to screen gene banks e.g. via PCR.

2 peptides NP 23 and NP 86 are for example particularly suitable from which the following primers can be derived:

peptide NP 23 (SEQ ID NO:8)
primer NP 23F (SEQ ID NO:9)
primer NP 23R (SEQ ID NO:6)
peptide NP 86 (SEQ ID NO:10)
primer NP 86-1F (SEQ ID NO:11)
primer NP 86-1R (SEQ ID NO:12)

Since the position of the two peptides relative to one another is not known at the start of the experiments, two different primer combinations have to be used in order to amplify a PCR fragment of the respective gene from the genomic DNA of *Clostridium histolyticum*: 23F/86-1R and 23R/86-1F. One of these combinations should result in a fragment in PCR if the experiment has been successful, the second combination then at the same time represents a negative control.

It is in fact possible to obtain a fragment of ca. 320 bp in length using primers NP 23F and NP 86-1R after PCR using DNA from *Clostridium histolyticum* isolated by conventional methods. The combination 23R/86-1F does not result in a fragment.

This ca. 320 bp fragment can readily be labelled, for example also in a PCR reaction, with dig-dUTP and serves as a probe to identify positive clones from a gene bank. The gene bank can be prepared according to generally known methods from *Clostridium histolyticum* DNA after digestion with restriction enzymes.

The ca. 320 bp fragment was sequenced and contains DNA of sequence SEQ ID NO: 2. This sequence is also present in the plasmid pNP-86-1R/23F which has been deposited on the Dec. 9, 1994 at the "Deutsche Sammlung von Mikroorganismen und Zellkulturen GmbH", Mascheroder Weg 1b, 38124 Braunschweig (DSM) under the no. 9578.

Genomic DNA from *Clostridium histolyticum* was digested with HindIII and subsequently the fragments were ligated with DNA ligase. Two outwardly directed primers NPC5 (SEQ ID NO:5) and NP6C (SEQ ID NO:15) were derived from the 320 bp fragment and used in a PCR reaction. A 586 bp fragment (SEQ ID NO:1) was obtained that contained most of SEQ ID NO:2. However, in this way it was not possible to find further parts of the gene for neutral protease.

The 586 bp fragment also contains further peptides from the protein digestion in addition to peptide NP23 and a portion of peptide NP86 which can be used to identify the reading frame.

NP-NT2: (SEQ ID NO:13)
NP58: (SEQ ID NO:14)

The PCR primer NP-19R (SEQ ID NO:17) was derived from a new peptide, NP19 (SEQ ID NO:16). A PCR reaction with primer NP-19R and primer 416 (SEQ ID NO:18) which had been derived from the 320 bp fragment yielded a 488 bp fragment that contained further sequence information of the neutral protease (ca. 350 bp more than SEQ ID NO:2). Since the reading frame at the 3' end was still open, a further small part of the gene had to be still missing. It was already possible to establish a rough restriction map (FIG. 1) by mapping the region of the neutral protease gene with the aid of Southern analyses.

In order to isolate the complete 3' end of the neutral protease gene, the genomic DNA from *Clostridium histolyticum* was cleaved with EcoRV and ScaI, the fragments were separated in an Agarose gel and analysed by means of Southern blot. Fragments of about 1000 bp in size were isolated from the gel since such a section of DNA should contain the residual 3' sequence based on the restriction map. The DNA fragments isolated from the gel were ligated (blunt end). An inverse PCR was again carried out using the outwardly directed primers 428 (SEQ ID NO:19) and 429 (SEQ ID NO:20) and a DNA fragment of 950 bp in size was obtained which contained the 3' end of the neutral protease gene as well as a further 470 bp downstream sequence. Thus the neutral protease gene was complete isolated (SEQ ID NO:3).

The plasmid pUC21-E-NP that contains the bases 933–2100 of SEQ ID NO:3 was deposited on the Nov. 23, 1995 at the "Deutsche Sammlung von Mikroorganismen und Zellkulturen GmbH", Mascheroder Weg 1b, D-38124 Braunschweig under the no. DSM 10341.

EXAMPLE 3

Expression of neutral protease

DNA fragments which contain the gene for neutral protease or parts thereof are modified at their ends in a suitable manner (e.g. via PCR) and they are used as a whole or in combination in an expression vector for *E. coli*. Those promoters that can be well regulated are preferably used such as e.g. lac, tac, trc, mgl; however, the use of other promoters is also conceivable. For the secretion the own signal peptide of neutral protease or a heterologous one (such as e.g mgl, PhoA) can be used.

An *E. coli* strain which has been transformed with an expression plasmid is either cultured overnight at 30° or 37° C. (e.g. in 5 ml culture) in minimum medium or LB medium under antibiotic selection. The overnight culture is inoculated into a larger volume (e.g. 1 l) and allowed to grow further. If this volume is already used to obtain biomass, it can for example be induced at an $OD_{550}$ of 0.2 to 2 with IPTG when using a lac promoter and the cells are allowed to grow further until there is no further increase in the OD and/or the enzyme activity that forms. At this time it is centrifuged and the biomass is used to purify neutral protease. However a significant proportion of the neutral protease activity may be present in the medium; then the medium is also collected and neutral protease is purified therefrom.

EXAMPLE 4

Islet isolation from porcine pancreas

The pancreas is prepared from a freshly slaughtered pig and cooled in ice-cold HBSS buffer (Gibco) until further processing. A Braunüle is inserted into the ductus pancreaticus and fastened there, the water-tightness of the pancreas is tested using HBSS buffer. An enzyme solution in HBSS buffer+$Ca^{2+}$ which contains purified recombinant neutral protease alone from *Clostridium histolyticum* or in a mixture with a purified collagenase type I or II is injected. The pancreas treated in this way is connected to the perfusion unit that also contains the above-mentioned enzyme solution (discontinuous perfusion). The digestion is carried out between 4° C. and 37° C. during a time period of 5 to 120 minutes during which the enzyme solution present in the vessel is continuously pumped into the pancreas. The pump is stopped after the time that is assumed to be optimal (usually 20 to 30 minutes until the islets are released) and the vessel containing the pancreas is carefully shaken for 3 to 20 minutes by hand. The prior addition of metal balls additionally facilitates the mechanical dissociation of the tissue and release of the islets from the surrounding exocrine tissue. The progress of the digestion is monitored microscopically after dithiozone staining of samples taken at regular intervals.

The digestion is stopped by addition of ice-cold HBSS/10% FCS (foetal calf serum) and the suspension is filtered through a sieve (mesh size 300 μm) in order to separate coarse particles. The islets present in the filtrate are centrifuged for 10 minutes at 100 g in 250 ml Nalgene round-bottom flasks. The supernatant is decanted and the pellet containing the islets is resuspended in 50 ml FCS.

The islets can be purified further by means of a density gradient made by hand. Firstly 7 ml islet suspension is added to 250 ml Nalgene round-bottom flasks. These are firstly overlayered with 93 ml of a Ficoll® solution ($\phi$=1.077 g/cm3), and then with 50 ml medium (RPMI 1640). These gradients are centrifuged for 10 minutes at 100 g in a swing-out rotor. Fractions of 10 ml are collected, the size, purity and yield of the islets stained with dithiozone is determined microscopically in every fraction or with the aid of image analysis.

List of references

Aman et al., Gene 40 (1985) 183
Brosius et al., J. Mol. Biol. 148 (1981) 107–127
Chang et al., Nature 198 (1977) 1056
Davies et al., Ann. Rev. Microbiol. 32 (1978) 469
EP-A-0 267 851
EP-A 0 495 398
French M. F. et al., J. Protein Chemistry 11 (1992) 83–97
Ghrayeb et al., EMBO J. 3 (1984) 2437
Goeddel et al., Nuc. Acids Res. 8 (1980) 4057
Hames, B. D., S. G. Higgins, Nucleic Acid Hybridization—A practical approach (1985), IRL-Press, Oxford, England
Haworth et al., Cell Calcium 10, 1989, 57–62
Hefley et al., Exp. Cell Res. 149, 1983, 227–236
Hefley et al., J. Bone Mineral Res. 2 (1987) 505–516
Holzinger et al., Immunology Letters 35, 1993, 109–118
Kaunitz, Am. J. Physiol. 254, 1988, 6502–6512
Kingsman S. M. et al, Tibtech 5 (1987) 53–57
Mandl et al., J. Clin. Invest 32, 1953, 1323–1329
Marcus et al., Endocrine Res. 10, 1984, 151–162
Maruyama et al., J. Pharmacol. Methods 19, 1988, 155–164
Miller et al., Bio/Technology 7 (1989) 698
Morrish & Siy, Endocrine Res. 12, 1986, 229–253
Nagai et al., Nature 309 (1984) 810
Oka et al., Proc. Natl. Acad. Sci. USA 82 (1985) 7212
Palva et al., Proc. Natl. Acad. Sci. USA 79 (1982) 5582
Phillips and Silhavy, Nature 344 (1990) 882–884
Powell et al., Appl. Environ. Microbiol. 54 (1988) 655
Quibel et al., Anal. Biochem. 154 (1986) 26–28
Ricordi et al, Diabetes 37 (1988) 413–420
Sambrook et al., "Expression of cloned genes in *E. coli*" in Molecular Cloning: A laboratory manual (1989) Cold Spring Harbor Laboratory Press, New York, USA
Sambrook J. et al., Molecular Cloning: a laboratory manual (1989), Cold Spring Harbor Laboratory Press, New York, N.Y.
Shimatake et al., Nature 292 (1981) 128
Sparrow & McQuade, Biochim. Biophys. Acta 302, 1973, 90–94
Studier et al., J. Mol. Biol. 189 (1986) 113
Sutton et al., Transplantation 42 (1986) 689–691
U.S. Pat. No. 4,551,433
U.S. Pat. No. 4,689,406
U.S. Pat. No. 4,747,056
Vendrell & Alemany, J. Biochem. Biophys. Methods 16, 1988, 49–54
WO 91/11520
Wolters et al., Diabetologica 35, 1992, 735–742
Wolters, Hormone and Metabolic Research 26 (1994) p. 80
Yansura, Meth. Enzymol. 185 (1990) 161–166

We claim:

1. An isolated nucleic acid selected from the group consisting of
   a) a DNA of nucleotides 1027–1965 of SE ID NO:3 or a DNA which is complementary thereto,
   b) a nucleic acid which hybridizes under low stringency conditions with a DNA of nucleotides 1027–1965 of SEQ ID NO:3,
   c) a nucleic acid which encodes for the same amino acid sequence as depicted in SEQ ID NO:5;
wherein the nucleic acid codes for a protein with the activity of neutral protease from *Clostridium histolyticum*.

2. The nucleic acid of claim 1 comprising nucleotides 1027–1965 of SEQ ID NO:3.

3. The nucleic acid of claim 1 comprising nucleotides 970–1965 of SEQ ID NO:3.

4. A recombinant vector comprising the nucleic acid of claim 1 operably linked to expression sequences.

5. A prokaryotic or eukaryotic host cell which is stably transformed or transfected with the recombinant vector of claim 4.

6. A process for the production of a polypeptide which has the properties of a neutral protease from *Clostridium histolyticum*, said process comprising:
   a) expressing an exogenous nucleic acid in prokaryotic or eukaryotic host cells, and
   b) isolating the desired polypeptide,
wherein the nucleic acid codes for a protein with the activity of neutral protease from *Clostridium histolyticum* and is selected from the group consisting of:
   i) a DNA of nucleotides 1027–1965 of SEQ ID NO:3 or a DNA which is complementary thereto,
   ii) a nucleic acid which hybridizes under low stringency conditions with a DNA of nucleotides 1027–1965 of SEQ ID NO:3,
   iii) a nucleic acid which encodes for the same amino acid sequence as depicted in SEQ ID NO:5.

7. The process of claim 6, wherein the nucleic acid is a DNA of nucleotides 1027–1965 of SEQ ID NO:3.

8. The process of claim 6, wherein the host cells are *E. coli*.

9. The process of claim 6, wherein the host cells are yeast cells or insect cells.

10. A purified polypeptide with the activity of neutral protease of *Clostridium histolyticum* which is free of other proteins from *Clostridium histolyticum* wherein said polypeptide is prepared according to the process of claim 6.

11. A process for disintegrating cell tissue and releasing cells or groups of cells contained therein, comprising incubating a) the cell tissue with the purified polypeptide of claim 10 until the cells or groups of cells have been released to the desired extent and b) separating the cells or groups of cells from the cell tissue fractions.

12. The process of claim 11, wherein the separation is achieved by a density gradient centrifugation.

13. The process of claim 11, wherein the cell tissue is selected from the group consisting of liver, skin, umbilical cord, endothelial, bone, muscle, heart, ovarian, uterus, fat and placental tissue.

14. The process of claim 11, wherein the cell tissue is tumor tissue.

15. The process of claim 11, wherein the cell tissues are pancreatic tissue, the isolated cells are islet cells and the groups of cells are islets.

16. An isolated nucleic acid which hybridizes under high stringency conditions with nucleotides 1027–1965 of SEQ ID NO:3, wherein the nucleic acid encodes a protein having the activity of neutral protease derived from *Clostridium histolyticum*.

17. A process for the production of a polypeptide having the activity of neutral protease derived from *Clostridium histolyticum*, said process comprising
   a) expressing an exogenous nucleic acid in prokaryotic or in eukaryotic host cells, and
   b) isolating the polypeptide therefrom,
   wherein the nucleic acid hybridizes under high stringency conditions with nucleotides 1027–1965 of SEQ ID NO:3.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 586 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
AAGCTTCATT  TTGGCATATG  TTTGTARGTG  CTGAAAATGG  AAAGATAGTG  GATAAGTATA        60

ATGCTTTATC  ATGCCAAGCT  ACACATGCTC  AAGTAAGAGG  AGTTAATAGC  AGTGGAGAGC       120
```

| | | | | | | |
|---|---|---|---|---|---|---|
|ATAAAATCCT|AAATGGTATG|TTTGAAAATG|GAAGATATTT|TTTAGCAGAT|TCCACCAGAC|180|
|CTTCAAATGG|ATATATATTA|ACATATGATG|CTAATAACCA|AGAGTATGGT|TTCCCAGGTA|240|
|GCTTATTTAG|TAATTTAACA|GGCATTTTTC|GTAGTGATAG|ACCAAAGGCA|GGAGTAGATG|300|
|CTCACCATAA|TCTAACTCMA|GTATATGATT|ATTATAAAAA|TGTTTTAAAT|AGAGATAGTT|360|
|TTGATGGAAA|AGGTGCTAGT|ATAATATCTT|CTGTGCATTG|TAGGAAATAA|TTTAAATAAT|420|
|GCTTTCTGGA|ATGGTAGACA|AATACTTTTT|GGTGATGGAG|ACGGAGTTAC|ATTTAGTAAC|480|
|CTAGCAAAAT|GTTTAGAAGT|TACTGCCCAT|GAATTACAC|ATGCAGTTAC|TCAAAGTACT|540|
|GCAGGTCTAG|AATATAGATT|TCAATCTGGT|GCTCTAAATG|AAGCTT| |586|

( 2 ) INFORMATION FOR SEQ ID NO: 2:

( i ) SEQUENCE CHARACTERISTICS:
        ( A ) LENGTH: 329 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 2:

| | | | | | | |
|---|---|---|---|---|---|---|
|GGCAGGAGTA|GATGCTCACC|ATAATCTAAC|TCMAGTATAT|GATTATTATA|AAAATGTTTT|60|
|AAATAGAGAT|AGTTTTGATG|GAAAAGGTGC|TAGTATAATA|TCTTCTGTGC|ATTGTAGGAA|120|
|ATAATTTAAA|TAATGCTTTC|TGGAATGGTA|GACAAATACT|TTTTGGTGAT|GGAGACGGAG|180|
|TTACATTTAG|TAACCTAGCA|AAATGTTTAG|AAGTTACTGC|CCATGAATTT|ACACATGCAG|240|
|TTACTCAAAG|TACTGCAGGT|CTAGAATATA|GATTTCAATC|TGGTGCTCTA|AATGAAGCTT|300|
|TTTCTGATAT|TTTAGGTATA|GCTGTTCAC| | | |329|

( 2 ) INFORMATION FOR SEQ ID NO: 3:

( i ) SEQUENCE CHARACTERISTICS:
        ( A ) LENGTH: 2428 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: sig_peptide
        ( B ) LOCATION:970..1026

( i x ) FEATURE:
        ( A ) NAME/KEY: mat_peptide
        ( B ) LOCATION:1027..1965

( x i ) SEQUENCE DESCRIPTION: SEQ ID NO: 3:

| | | | | | | |
|---|---|---|---|---|---|---|
|GACTCTATTG|GAGCACTAAT|AGGAATTATA|ATTATAACAA|TTTTATTTAG|AAAGAAAAT|60|
|GGTTAGAGAG|CTTGCTATGA|CTTATGTTAT|ATGTCATAGC|ATTTTTGTTT|TATAAGAGGA|120|
|TTATTAGGAA|ATATTACGGG|AATCAAAATA|AAATCAATAG|AATTTAATGT|AAATTTTAAC|180|
|TTAAAAATAT|AAACTGAATA|TAAAATATAC|AAAAACCGGA|AATAATTAG|TGAGAATGTT|240|
|GAGAAAAATT|ACAAAAGTG|TATNTACTTT|ACCATTTATT|AGTACTACAA|TAGGGTTATA|300|
|AATAATAAMG|AGGAGGAGTA|AAATGAAAAA|AAATTTNNNN|NNNNNNNNN|NNNNNNNNN|360|
|NNNNNNNNN|NNNNNNNNN|NNNNNNNNN|NNNNNNNNN|NNNNNNNNN|NNNNNNNNN|420|
|NNNNNNNNN|NNNNNNNNN|NNNNNNNNN|NNNNNNNNN|NNNNNNNNT|GCTCTAAATG|480|
|AAGCTTTTTC|TGTATTAAAA|ACAGATTTAG|AAAAAACCAA|GAATATAAAA|TCTAATAATA|540|

```
AGGAGGGGGA  TGATGTAACA  AAAGTAGTTA  AGAGTGCTTT  AAAAGAAGAA  GCCAATTTAG   600
GAGATTTTAA  GGGTTGATAA  TAAAGAAACT  GATGTAAAAG  GTAAAAAGCA  CTTGCGTTTC   660
ACAAATGTTA  TAGATGGTAT  TCCTGTATAT  GGTAGTCAAG  TTATAATTCA  TACTAATAAA   720
GATGGACAAG  TATATAGCGT  AAATGGAAAA  GTAGATAAAC  AGCCTAAAGC  TCAATCTTTT   780
AAGAACCGTG  TAAGGATTAA  GGACGATAAA  GCTATTAAAA  TAGCAGAAGA  CAGTTTAGGT   840
AAGGAAATAA  AGAAAACAA   AAATTATCAT  TCTGAAAGTA  AGTTGTACCT  ATACAAGGTT   900
AATGGAGATT  TGCAACCTGT  GTATTTGGTA  AAGATATCAT  CTACAGAACC  AGAAGCTTCA   960
TTTTGGCATA  TGTTTGTAAG  TGCTGAAAAT  GGAAAGATAG  TYGATAAGTA  TAATGCTTTA  1020
TCATGCCAAG  CTACACATGC  TCAAGTAAGA  GGAGTTAATA  GCAGTGGAGA  GCATAAAATC  1080
TTAAATGGTA  TGTTTGAAAA  TGGAAGATAT  TTTTAGCAG   ATTCAACAAG  ACCTTCAAAT  1140
GGATATATAT  TAACATATGA  TGCTAATAAC  CAAGAGTATG  GTTTCCCAGG  TAGCTTATTT  1200
AGTAATTTAA  CAGGCATTTT  TCGTAGTGAT  AGACAAAAGG  CAGGAGTAGA  TGCTCACCAT  1260
AATCTAACTC  AAGTATATGA  TTATTATAAA  AATGTTTTAA  ATAGAGATAG  TTTTGATGGA  1320
AAAGGTGCTA  GTATAATATC  TTCTGTGCAT  GTAGGAAATA  ATTTAAATAA  TGCTTTCTGG  1380
AATGGTAGAC  AAATACTTTT  TGGTGATGGA  GACGGAGTTA  CATTAGTAA   CCTAGCAAAA  1440
TGTTTAGAAG  TTACTGCCCA  TGAATTTACA  CATGCAGTTA  CTCAAAGTAC  TGCAGGTCTA  1500
GAATATAGAT  TTCAATCTGG  TGCTCTAAAT  GAAGCTTTTT  CTGATATTTT  AGGTATAGCT  1560
GTTCACAGTG  ATCCAAATGA  TTGGGAAATT  GGAGAAGATA  TATACACTCC  TAATGTAGCA  1620
GGAGATGCTT  TAAGAAGTAT  GTCAAATCCT  AGATTATATA  GACAACCAGA  CCATATGAAG  1680
GACTATTTAT  ATTGGGATTA  TTCAATGGAT  AAAGGTGGAG  TTCATTATAA  TTCAGGTATT  1740
CCAAATAAAG  CAGCTTATTT  GATGGGAAAA  GAAGTTGGAA  AAGATTCAAT  GGCTAAAATT  1800
TATTATCATG  CTTTAGTGAA  TTATTTAACT  CCTCAAAGTA  CATTTGAAGA  TGCTAGAAAT  1860
GCAGTAGTAT  CATCTGCAAT  AGATTTACAT  GGTGAGAATA  GTAAAGAACA  TAAACTTGCT  1920
ATAAAATCTT  GGGCAGATGT  AGGAGTTGGA  GAAGAGGCAG  TAAGATAATA  GAGAATATGA  1980
AGGATTCCAT  TATAATAAAT  ATATAATGCC  TGTTTTTGAT  AGATTAAGTA  ATACCATAAA  2040
GTAGAGAATA  TAAAAAATAA  AAATCTACTG  CATTGTATTT  TAGATAAATA  GGTGCGGAAT  2100
ATAGAACAAG  CTAAMTTATA  TTAAAAATAA  GTATAGGAAT  ATAATTAATA  GGTAAGGTAA  2160
ATCATTTTTC  TAAGGTAGTT  GCAGTAGGTA  GTATAAAGTA  TTAGTAGTAG  AGTATATTAG  2220
TTAAAGGAAA  AAATCCCTCA  CATATAAAAA  TACGCTATGT  ATATTTGTTA  CCTAAAAATT  2280
GAATTATAAA  AAAAAGGTGT  CTGRAGGCTA  ADATAAAACC  TTTCGGCACC  TTTTTACATT  2340
ACCAGTTATT  ATAGTGGATY  CTTTCTTTAT  CCAATCTATC  GTAATGTTTT  TTTTCYTCAT  2400
TAGGATACTG  CAGGTCTAGA  ATATAGAT                                       2428
```

( 2 ) INFORMATION FOR SEQ ID NO: 4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 4:

Tyr  Tyr  His  Ala  Leu  Val  Asn  Tyr
    1                  5

( 2 ) INFORMATION FOR SEQ ID NO: 5:

( i ) SEQUENCE CHARACTERISTICS:
        ( A ) LENGTH: 313 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 5:

```
Gln Ala Thr His Ala Gln Val Arg Gly Val Asn Ser Ser Gly Glu His
  1               5                  10                  15
Lys Ile Leu Asn Gly Met Phe Glu Asn Gly Arg Tyr Phe Leu Ala Asp
             20                  25                  30
Ser Thr Arg Pro Ser Asn Gly Tyr Ile Leu Thr Tyr Asp Ala Asn Asn
         35                  40                  45
Gln Glu Tyr Gly Phe Pro Gly Ser Leu Phe Ser Asn Leu Thr Gly Ile
     50                  55                  60
Phe Arg Ser Asp Arg Gln Lys Ala Gly Val Asp Ala His His Asn Leu
 65                  70                  75                  80
Thr Gln Val Tyr Asp Tyr Tyr Lys Asn Val Leu Asn Arg Asp Ser Phe
                 85                  90                  95
Asp Gly Lys Gly Ala Ser Ile Ile Ser Ser Val His Val Gly Asn Asn
            100                 105                 110
Leu Asn Asn Ala Phe Trp Asn Gly Arg Gln Ile Leu Phe Gly Asp Gly
        115                 120                 125
Asp Gly Val Thr Phe Ser Asn Leu Ala Lys Cys Leu Glu Val Thr Ala
    130                 135                 140
His Glu Phe Thr His Ala Val Thr Gln Ser Thr Ala Gly Leu Glu Tyr
145                 150                 155                 160
Arg Phe Gln Ser Gly Ala Leu Asn Glu Ala Phe Ser Asp Ile Leu Gly
                165                 170                 175
Ile Ala Val His Ser Asp Pro Asn Asp Trp Glu Ile Gly Glu Asp Ile
            180                 185                 190
Tyr Thr Pro Asn Val Ala Gly Asp Ala Leu Arg Ser Met Ser Asn Pro
        195                 200                 205
Arg Leu Tyr Arg Gln Pro Asp His Met Lys Asp Tyr Leu Tyr Trp Asp
    210                 215                 220
Tyr Ser Met Asp Lys Gly Gly Val His Tyr Asn Ser Gly Ile Pro Asn
225                 230                 235                 240
Lys Ala Ala Tyr Leu Met Gly Lys Glu Val Gly Lys Asp Ser Met Ala
                245                 250                 255
Lys Ile Tyr Tyr His Ala Leu Val Asn Tyr Leu Thr Pro Gln Ser Thr
            260                 265                 270
Phe Glu Asp Ala Arg Asn Ala Val Val Ser Ser Ala Ile Asp Leu His
        275                 280                 285
Gly Glu Asn Ser Lys Glu His Lys Leu Ala Ile Lys Ser Trp Ala Asp
    290                 295                 300
Val Gly Val Gly Glu Glu Ala Val Arg
305                 310
```

( 2 ) INFORMATION FOR SEQ ID NO: 6:

( i ) SEQUENCE CHARACTERISTICS:
        ( A ) LENGTH: 20 base pairs
        ( B ) TYPE: nucleic acid (C) STRANDEDNESS: single
(D) TOPOLOGY: linear (i i) MOLECULE TYPE: other nucleic acid
    (A) DESCRIPTION: /desc = "Primer 23R"

(x i) SEQUENCE DESCRIPTION: SEQ ID NO: 6:

TGNGTNARRT TRTGRTGNGC          20

(2) INFORMATION FOR SEQ ID NO: 7:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "Primer NPC5"

(x i) SEQUENCE DESCRIPTION: SEQ ID NO: 7:

GTGATGGAGA CGGAGTTAC          19

(2) INFORMATION FOR SEQ ID NO: 8:

(i) SEQUENCE CHARACTERISTICS:
    (A) LENGTH: 16 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO: 8:

Gly Val Ala Ala His His Asn Leu Thr Gln Val Tyr Asp Tyr Tyr Lys
1               5                   10                  15

(2) INFORMATION FOR SEQ ID NO: 9:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "Primer 23F"

(x i) SEQUENCE DESCRIPTION: SEQ ID NO: 9:

GCNCAYCAYA AYYTNACNCA          20

(2) INFORMATION FOR SEQ ID NO: 10:

(i) SEQUENCE CHARACTERISTICS:
    (A) LENGTH: 24 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO: 10:

Ile Ala Val His Ser Asp Pro Asn Asp Trp Glu Ile Gly Glu Asp Ile
1               5                   10                  15

Tyr Thr Pro Asn Val Ala Gly Asp
                20

(2) INFORMATION FOR SEQ ID NO: 11:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: other nucleic acid
: ( A ) DESCRIPTION: /desc = "Primer 86-1F"

( x i ) SEQUENCE DESCRIPTION: SEQ ID NO: 11:

GAYCCNAAYG AYTGGGARAT 20

( 2 ) INFORMATION FOR SEQ ID NO: 12:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: other nucleic acid
: ( A ) DESCRIPTION: /desc = "Primer 86-1R"

( x i ) SEQUENCE DESCRIPTION: SEQ ID NO: 12:

ATYTCCCART CRTTNGGRTC 20

( 2 ) INFORMATION FOR SEQ ID NO: 13:

( i ) SEQUENCE CHARACTERISTICS:
: ( A ) LENGTH: 18 amino acids
: ( B ) TYPE: amino acid
: ( C ) STRANDEDNESS: single
: ( D ) TOPOLOGY: linear ( i i ) MOLECULE TYPE: peptide ( x i ) SEQUENCE DESCRIPTION: SEQ ID NO: 13:

Ala Thr His Ala Xaa Val Arg Gly Val Asn Ser Ser Gly Glu His Lys
1               5                   10                  15

Ile Leu ( 2 ) INFORMATION FOR SEQ ID NO: 14:

( i ) SEQUENCE CHARACTERISTICS:
: ( A ) LENGTH: 16 amino acids
: ( B ) TYPE: amino acid
: ( C ) STRANDEDNESS: single
: ( D ) TOPOLOGY: linear ( i i ) MOLECULE TYPE: peptide ( x i ) SEQUENCE DESCRIPTION: SEQ ID NO: 14:

Phe Thr His Ala Val Thr Gln Ser Thr Ala Gly Leu Glu Tyr Arg Asp
1               5                   10                  15

( 2 ) INFORMATION FOR SEQ ID NO: 15:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: other nucleic acid
: ( A ) DESCRIPTION: /desc = "Primer NPC6"

( x i ) SEQUENCE DESCRIPTION: SEQ ID NO: 15:

TGTCTACCAT TCCAGAAAGC 20

( 2 ) INFORMATION FOR SEQ ID NO: 16:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 16:

Ser Trp Ala Asp Val Gly Val Gly Glu Glu Ala
1               5                   10

( 2 ) INFORMATION FOR SEQ ID NO: 17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer 19-R"

( x i ) SEQUENCE DESCRIPTION: SEQ ID NO: 17:

GCYTCYTCNC CNACNCCTA                                       19

( 2 ) INFORMATION FOR SEQ ID NO: 18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer 416"

( x i ) SEQUENCE DESCRIPTION: SEQ ID NO: 18:

GTTACTCAAA GTACTGCAGG                                      20

( 2 ) INFORMATION FOR SEQ ID NO: 19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer 428"

( x i ) SEQUENCE DESCRIPTION: SEQ ID NO: 19:

CTTGCTATAA AATCTTGGGC                                      20

( 2 ) INFORMATION FOR SEQ ID NO: 20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer 429"

( x i ) SEQUENCE DESCRIPTION: SEQ ID NO: 20:

AAAGCTTCAT TTAGAGCACC C                                     21